(12) United States Patent
Shioyama et al.

(10) Patent No.: US 9,658,214 B2
(45) Date of Patent: May 23, 2017

(54) METHOD AND APPARATUS FOR ANALYZING CELLS

(71) Applicant: NIHON KOHDEN CORPORATION, Tokyo (JP)

(72) Inventors: Takahiro Shioyama, Tokyo (JP); Akane Suzuki, Tokyo (JP); Hirotsugu Kubo, Tokyo (JP); Sunao Takeda, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 882 days.

(21) Appl. No.: 13/946,849

(22) Filed: Jul. 19, 2013

(65) Prior Publication Data
US 2014/0030728 A1   Jan. 30, 2014

(30) Foreign Application Priority Data

Jul. 24, 2012 (JP) ................................. 2012-163969

(51) Int. Cl.
| | | |
|---|---|---|
| G01N 33/50 | (2006.01) | |
| G01N 33/574 | (2006.01) | |
| G01N 15/14 | (2006.01) | |
| G01N 21/64 | (2006.01) | |

(52) U.S. Cl.
CPC ..... *G01N 33/5091* (2013.01); *G01N 15/1429* (2013.01); *G01N 33/574* (2013.01); *G01N 33/57496* (2013.01); *G01N 21/6428* (2013.01)

(58) Field of Classification Search
CPC ............................................... G01N 33/5091
USPC .......................................................... 702/21
See application file for complete search history.

(56) References Cited

U.S. PATENT DOCUMENTS

| | | |
|---|---|---|
| 2005/0221399 A1 | 10/2005 | Nakano et al. |
| 2012/0034605 A1 | 2/2012 | Hinoda et al. |
| 2012/0052491 A1 | 3/2012 | Shioyama et al. |
| 2012/0076725 A1 | 3/2012 | Birse et al. |
| 2013/0090258 A1 | 4/2013 | Kanoaka et al. |

FOREIGN PATENT DOCUMENTS

| | | |
|---|---|---|
| CN | 1074365 A | 7/1993 |
| CN | 103060327 A | 4/2013 |
| JP | 2005-315862 A | 11/2005 |
| JP | 2011-527414 A | 10/2011 |
| JP | 2012-47594 A | 3/2012 |
| WO | 2010/113529 A1 | 10/2010 |
| WO | 2011/158667 A1 | 12/2011 |

OTHER PUBLICATIONS

The extended European Search Report for the related European Patent Application No. 13177448.1 dated Nov. 4, 2013.

S. Takeda et al.; "Flow cytometry as a diagnostic method for colorectal cancer;" Engineering in Medicine and Biology Society (EMBC); 2012 Annual International Conference of the IEEE; Aug. 28, 2012-Sep. 1, 2012; pp. 1004-1007; XP032463088.

A. Suzuki et al.; "A New Automatic Cell Isolation System for Flow Cytometry; Cell Isolation Unit and Staining Reagent Kit"; Engineering in Medicine and Biology Society (EMBC); 2012 Annual International Conference of the IEEE; Jun. 2, 2012; pp. 2412-2415; XP032463427.

Reuy-Bin Chen; "Flow Cytometric Analysis of Benign and Malignant Tumors of the Oral and Maxillofacial Region"; Journal of Oral and Maxillofacial Surgery; vol. 47, No. 6, Jun. 1, 1989; pp. 596-606; XP027055031.

Myriam Remmelink et al.; "Determination of DNA Ploidy, Nuclear Size, and Proliferative Activity by Means of the Computer-Assisted Image Analysis of Feulgen-Stained Nuclei in 68 Soft Tissue Tumors of Adults"; Human Pathology; vol. 25, No. 7, Jul. 1, 1994; pp. 694-701; XP026243039.

Robert P. Wersto et al.; "Flow Cytometric DNA Analysis of Human Solid Tumors: A Review of the Interpretation of DNA Histograms"; Human Pathology; vol. 22, No. 11, Nov. 1, 1991; pp. 1085-1098; XP026255636.

Database Compendex; Engineering Information, Inc., New York 2013; N. Hinata et al.; "A study on the method for cancer diagnosis using FFT on DNA ploidy analysis"; XP002714485.

Tokuhiko Ikeda; "Research on the Efficiency of Lung cancer CT screening"; cited in Japanese Office Action for the related Japanese Patent Application No. 2012-163969.

Japanese Office Action for the related Japanese Patent Application No. 2012-163969 dated Oct. 6, 2015.

Chinese Office Action issued in Chinese Patent Application No. 2013103140004 dated Nov. 1, 2016.

A. Suzuki, et al., "A New Automatic Cell Isolation System for Flow Cytomertry: Cell Isolation Unit and Staining Reagent Kit", 34th Annual International Conference of the IEEE Engineering in Medicine and Biology Society, Aug. 28, 2012, pp. 2412-2415, San Diego, CA.

(Continued)

*Primary Examiner* — Jerry Lin
(74) *Attorney, Agent, or Firm* — Pearne & Gordon LLP

(57) ABSTRACT

A method of analyzing cells, the method comprising: measuring a number of cells which are nuclear stained, in a to-be-determined tissue, and acquiring a histogram showing a fluorescence intensity based on a result of the measurement; analyzing the histogram, and acquiring data of predetermined parameters; comparing the data of the parameters with first thresholds predetermined for the parameters, to perform a first cancer determination for each of the parameters on the to-be-determined tissue; performing a scoring process for each of the parameters, on a result of the first cancer determination for each of the parameters, to calculate scores of the parameters; and combining the scores of the parameters with one another, thereby performing a second cancer determination on the to-be-determined tissue.

8 Claims, 12 Drawing Sheets

(56) References Cited

OTHER PUBLICATIONS

Japanese Office Action for Application No. 2012-163969 dated May 17, 2016.
Hirosumi Itoi, et al., "Analysis of DNA Ploidy Pattern", Clinical Gastroenterology, vol. 10, No. 12, pp. 1741-1748, 1995, Japan.
Keiji Kawamoto, et al., "Images of Laser Scanning Cytometer", Medical Imaging Technology, vol. 17, No. 3, pp. 197-202, 1999, Japan.

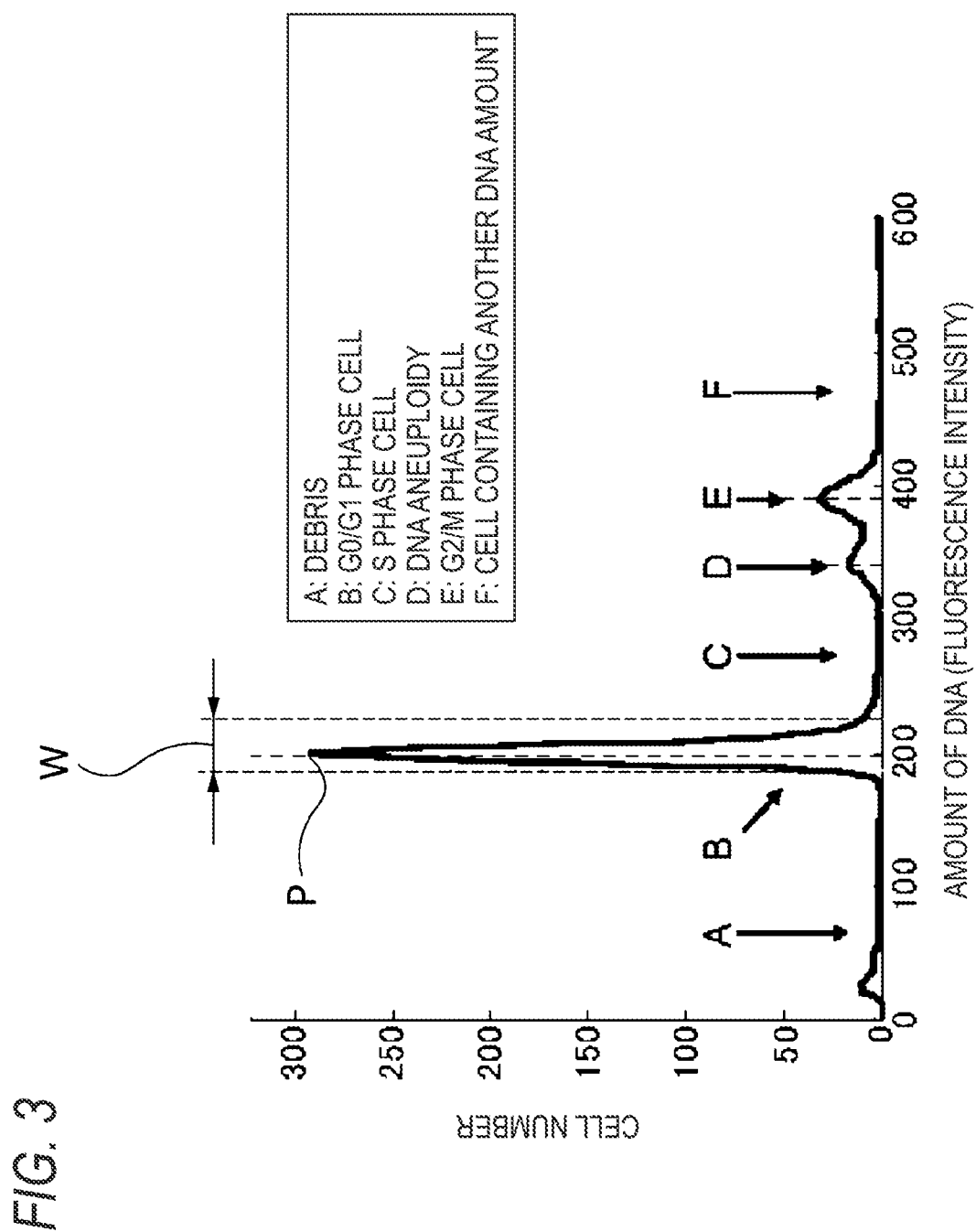

| SCORE | NORMAL | TUMOR |
|---|---|---|
| 6 |  | 6 |
| 5 | 1 | 11 |
| 4 | 1 | 4 |
| 3 | 1 | 4 |
| 2 | 8 | 1 |
| 1 | 9 |  |
| 0 | 6 |  |

METHOD AND APPARATUS FOR ANALYZING CELLS

CROSS-REFERENCE TO RELATED APPLICATION(S)

This application is based upon and claims the benefit of priority from prior Japanese patent application No. 2012-163969, filed on Jul. 24, 2012, the entire contents of which are incorporated herein by reference.

BACKGROUND

The presently disclosed subject matter relates to a cell analyzing method and cell analyzing apparatus which distinguish between normal and cancerous tissues.

After a pathological specimen is prepared, a pathological diagnosis on a tissue slice is performed by a cytotechnologist or a pathologist. A skilled technique is required for preparing a specimen or performing a diagnosis by a cytotechnologist or a pathologist, and there is a case where a difference may be produced in the diagnosis result depending on the difference in technique. In the period from extraction of a tissue to diagnosis, procedures such as tissue fixation, section preparation, and staining are necessary, and a cytotechnologist, a pathologist, or the like is restrained for a predetermined time period. Therefore, procedures which are to be performed before diagnosis are requested to be automatized.

Moreover, a determination whether a tissue extracted during an operation is a tumor tissue or a normal tissue is required depending on the portion of a tumor or the operative method. In the determination, a rapid diagnosis due to cytoscreening or a frozen slice is performed. As compared with a usual pathological analysis, however, higher skilled technique and diagnosis accuracy are requested. If an apparatus which performs objectively and rapidly a diagnosis whether tissue extracted during an operation is tumor (cancer cells) or not is developed, such an apparatus seems to be very useful for a pathologist.

Therefore, for example, an apparatus and method of analyzing cells have been proposed in which cells that are isolated and nuclear stained are measured to acquire a histogram of the fluorescence intensity, the number of strong-area cells that are distributed in an area where the fluorescence intensity is stronger than normal cells is obtained from data of the histogram, and the malignancy grade of cancer is determined based on the number of strong-area cells and the histogram (for example, see JP-A-2012-047594).

According to the apparatus and method of analyzing cells disclosed in JP-A-2012-047594, it is possible to determine the malignancy grade of cancer based on a histogram and the number of cells that are distributed in an area where the fluorescence intensity is stronger in the histogram. However, it is requested to perform more accurately the determination of cancerous tissues.

SUMMARY

The presently disclosed subject matter may provide a method and apparatus for analyzing cells which can distinguish more accurately cancerous tissues.

The method may comprise: measuring a number of cells which are nuclear stained, in a to-be-determined tissue, and acquiring a histogram showing a fluorescence intensity based on a result of the measurement; analyzing the histogram, and acquiring data of predetermined parameters; comparing the data of the parameters with first thresholds predetermined for the parameters, to perform a first cancer determination for each of the parameters on the to-be-determined tissue; performing a scoring process for each of the parameters, on a result of the first cancer determination for each of the parameters, to calculate scores of the parameters; and combining the scores of the parameters with one another, thereby performing a second cancer determination on the to-be-determined tissue.

The second cancer determination may be a determination that is performed by comparing an overall score in which the scores of the parameters are totalized, with a predetermined second threshold.

The second threshold may be a value of an overall score that, in the overall score which is previously acquired, in a ROC curve in which a sensitivity indicating a probability of correctly determining a cancer tissue, and a specificity indicating a probability of correctly determining a normal tissue are plotted, is determined in consideration of a balance between the sensitivity and the specificity.

The first thresholds may be values of analysis data that, in a large number of analysis data for the parameters which are previously acquired, in a ROC curve in which a sensitivity indicating a probability of correctly determining a cancer tissue, and a specificity indicating a probability of correctly determining a normal tissue are plotted, are determined in consideration of a balance between the sensitivity and the specificity.

The scoring process may be a process in which scoring is performed based on information of a result of the first cancer determination for each of the parameters.

In the scoring, weighting may be performed among the parameters based on a degree of contribution to the second cancer determination.

The parameters may include at least two or more of: a ratio of a number of all cells of a normal DNA amount to a number of all cells in the histogram; a ratio of a number of DNA amplified cells to a number of all cells in the histogram; a ratio of a debris number to a number of all cells in the histogram; a width of a peak of a normal distribution of cells of a normal DNA amount in the histogram; an area under a curve of a waveform which is obtained by performing a fast Fourier transform of the histogram; and a number of all cells in the histogram.

The apparatus may comprise: a flow cytometer which is configured to measure a number of cells which are nuclear stained, and which is configured to acquire a histogram showing a fluorescence intensity based on a result of the measurement; and an analysis controlling unit: which is configured to analyze the histogram acquired by the flow cytometer; and which is configured to acquire data of predetermined parameters; which is configured to perform a determination of a cancer or normal tissue, with respect to the acquired data based on thresholds predetermined for the parameters; which is configured to perform a scoring process for each of the parameters, on a result of determination of a cancer or normal tissue for each of the parameters, to calculate scores of the parameters; which is configured to combine the scores of the parameters with one another; and which is configured to perform a determination of a cancer or normal tissue based on the combined scores.

BRIEF DESCRIPTION OF THE DRAWINGS

FIG. 3 is a view showing an example of a DNA histogram acquired by a flow cytometer.

FIG. 4A shows a waveform obtained by FFT processing a DNA histogram of normal tissues, and FIG. 4B shows a waveform obtained by FFT processing a DNA histogram of cancer tissues.

DETAILED DESCRIPTION OF EXEMPLARY EMBODIMENTS

Hereinafter, an example of an embodiment of a method and apparatus for analyzing cells of the presently disclosed subject matter will be described with reference to the accompanying drawings.

Figure 1:
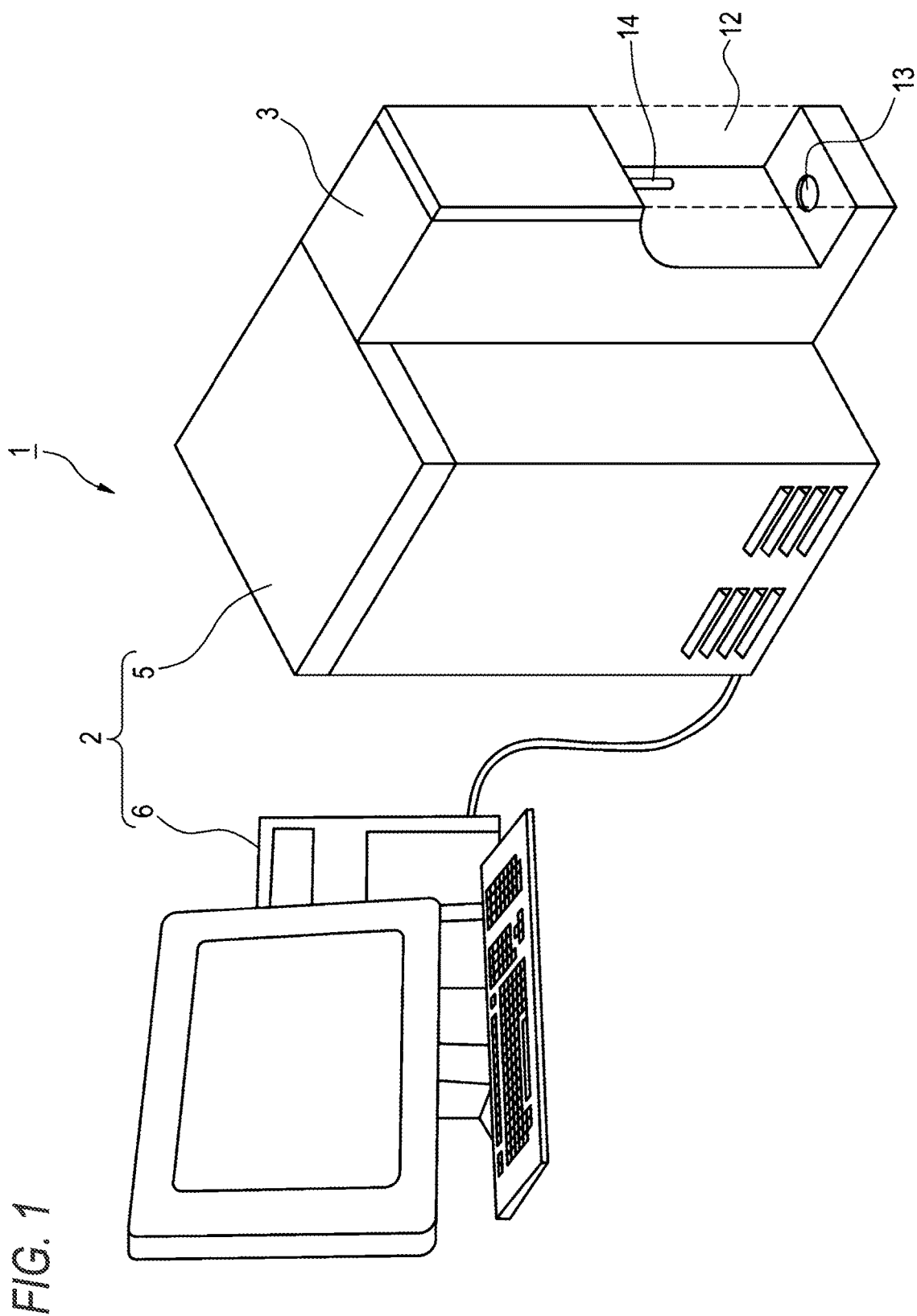
FIG. 1 is a diagram of a cell analysis system which includes an example of an embodiment of the apparatus for analyzing cells of the presently disclosed subject matter.

FIG. 1 shows a cell analysis system 1 for analyzing cells.

The cell analysis system 1 includes: a cell analyzing apparatus 2 having a flow cytometer 5 and a personal computer (hereinafter, often referred to also as an analysis controlling unit) 6; a cell pre-processing apparatus 3; and a cell isolation device 4 (see FIG. 2) which is set in the cell pre-processing apparatus 3.

The flow cytometer 5 of the cell analyzing apparatus 2 is an apparatus which is to be used in flow cytometry. Flow cytometry means a technique in which fine particles are dispersed in a fluid, and individual particles are optically analyzed while the fluid (suspending solution) is flown. The fine particles may be selectively recovered. In the embodiment, the flow cytometer 5 measures the number of cells which are nuclear stained, in the to-be-determined tissue,
and, by using a result of the measurement, acquires a DNA histogram (an example of a histogram) showing the fluorescence intensity.

The analysis controlling unit 6 of the cell analyzing apparatus 2 is an apparatus which analyzes the DNA histogram acquired by the flow cytometer 5.

Specifically, the analysis controlling unit 6 performs the following analyzing process.

For example, the analysis controlling unit 6 acquires data related to a plurality of parameters in order to obtain the feature of the DNA histogram. Moreover, the analysis controlling unit 6 compares the acquired data of the parameters with predetermined optimum thresholds of the parameters, and, with respect to each of the parameters, performs a cancer determination whether the to-be-determined tissue is a cancer tissue or a normal tissue.

With respect to results of the cancer determination for the parameters, moreover, the analysis controlling unit 6 performs a scoring process, i.e., scoring for each of the parameters. The analysis controlling unit 6 combines the scores for the parameters which are calculated in the scoring process, with one another to overall perform a cancer determination on the to-be-determined tissue.

The flow cytometer 5 and the analysis controlling unit 6 may be configured so as not to be formed as independent apparatuses, and may be formed as an integrated apparatus which has both the functions of the flow cytometer 5 and the analysis controlling unit 6.

The cell isolation device 4 is a tubular container into which the tissue to be analyzed is poured, and, when a cell isolation process is to be performed, set in the cell pre-processing apparatus 3. The cell pre-processing apparatus 3 is an apparatus for performing a pipetting process, and introduces and withdraws a cell treating chemical (containing a reagent) into and from the cell isolation device 4 through a nozzle.

Figure 2:
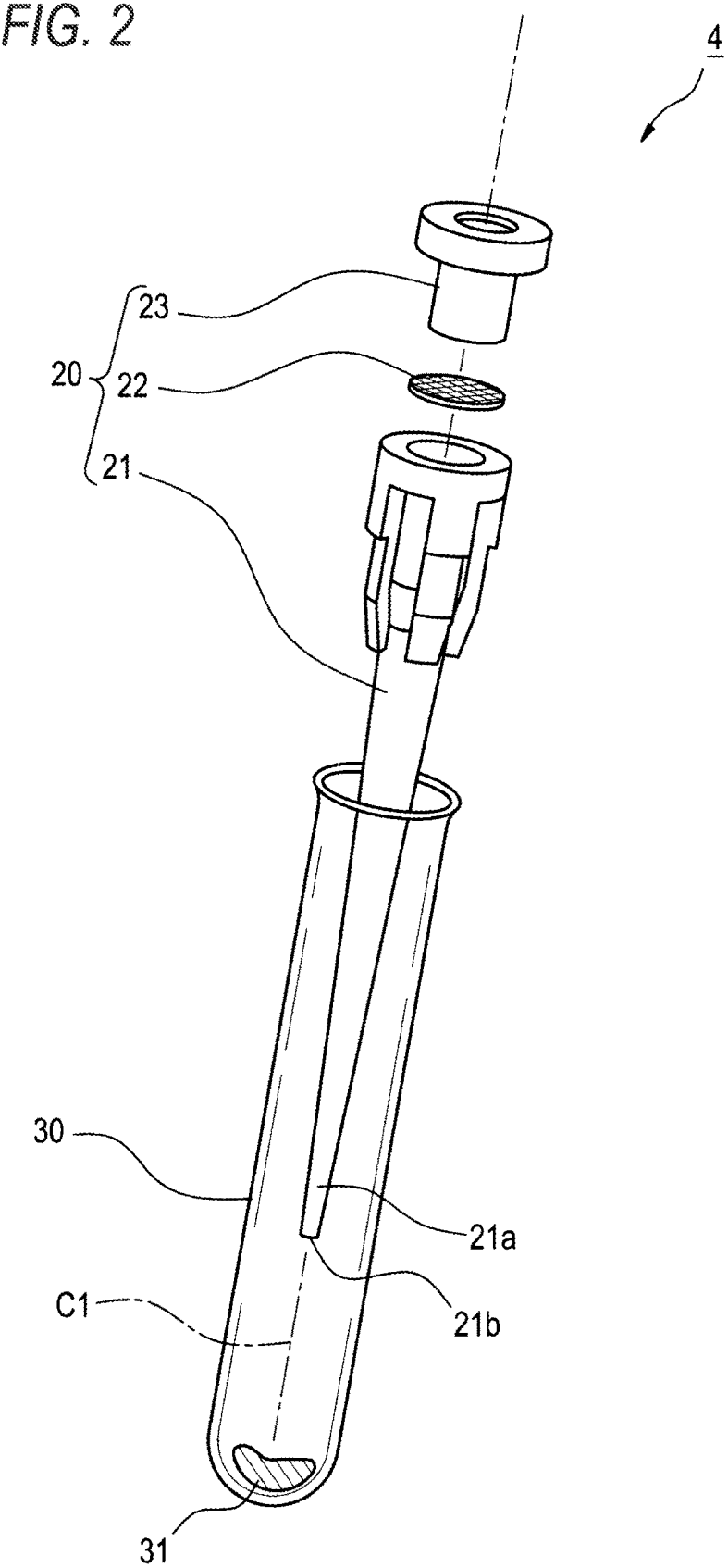
FIG. 2 is an exploded perspective view showing an example of a cell isolation device.

FIG. 2 shows the cell isolation device 4 in an exploded state.

The cell isolation device 4 includes a pipette member 20 having a body 21, a filter 22 (filter member), and a lid member 23, and a container 30.

A reagent 31 containing a surfactant, an RNA (ribonucleic acid) remover, and a fluorescent dye/pigment is accommodated on the bottom of the container 30 in a state where the reagent is dried or freeze-dried. When a tissue 30 which is to be subjected to the cell isolation process, and a cell treatment solution are loaded into the container 30, the reagent 31 dissolves in the cell treatment solution.

The cell isolation device 4 can execute nuclear isolation of tissue cells by the surfactant, RNA removal by the RNA remover, and staining of isolated DNA cell nuclei by the fluorescent dye/pigment, in parallel with a below-described cell isolation process by pipetting. This enables that, after recovery by the cell pre-processing apparatus 3, measurement by the flow cytometer 5 or the like is performed. Therefore, rapid diagnosis can be realized.

The pipette member 20 is attached to the container 30 in which the tissue and the cell treatment solution (containing the reagent 31) are accommodated. The tip end (opening 21b) of the body 21 is placed on the central axis C1 of the container 30, and opposed to the bottom of the container 30 via a constant gap. The loaded tissue is placed between the tip end of the body 21 and the bottom of the container 30. The tip end portion 21a of the body 21 is immersed in the loaded cell treatment solution.

Next, the contents of the cell isolation process in which the thus configured cell isolation device 4 is used, and which is performed by the cell pre-processing apparatus 3 will be described with reference to FIGS. 1 and 2.

A slide lid 12 of the cell pre-processing apparatus 3 is opened, and a bottom portion of the container 30 is inserted into a positioning hole 13 to support the container 30. An upper end portion of the cell isolation device 4 is connected to a lower end portion of a nozzle 14 of the cell pre-processing apparatus 3, and a passage of the nozzle 14 and the passage of the lid member 23 communicate with each other in an air- and liquid-tight manner through an adequate engagement structure. When the slide lid 12 of the cell pre-processing apparatus 3 is closed, the operation of the cell isolation process is started in the following procedure.

The cell pre-processing apparatus 3 includes a pump mechanism (not shown) which is connected to the nozzle 14. A controller of the cell pre-processing apparatus 3 controls the pump mechanism based on pipetting conditions (pipetting intensity, repetition number, duration, and the like) which are set by the user, to form a pressurized state and a depressurized state. In the pressurized state, air is blown out from the nozzle 14, and, in the depressurized state, air is sucked through the nozzle 14.

By performing the pipetting process in which a pressurized state and a depressurized state are repeatedly formed, the tissue and the cell treatment solution (containing the reagent 31) in the container 30 can be pipetted by means of the pipette member 20 connected to the nozzle 14.

When the pipetting process is performed for a predetermined time period, the tissue is gradually finely smashed to enter a minced state, the suspending solution containing isolated cells can be obtained. In this process, nuclei of cells are broken, and chromosomes therein are stained so as to respond to fluorescence.

Thereafter, the cell pre-processing apparatus 3 sucks the suspending solution in the container 30 through the passage in the pipette member 20. When the suspending solution passes through the filter 22, unwanted tissue pieces are filtered out, so that a cell suspension containing desired isolated cells is obtained. When the sucking operation is further continued, the cell suspension is recovered to the cell pre-processing apparatus 3, and then used in an analyzing process such as a fluorescence analysis by using the flow cytometer 5.

Next, a process of acquiring a DNA histogram (histogram acquiring step) performed by the flow cytometer 5 will be described.

By using the cell suspension, the flow cytometer 5 measures cells which are isolated and nuclear stained, and obtains a scattergram (not shown) in which relationships of related variables are displayed on a plane, from the peak value of a fluorescent signal at each event, and an integrated value. Then, an adequate gating process is performed on the scattergram to obtain a DNA histogram of integrated values of the fluorescence intensity from events which seem to be a single cell.

As described above, the flow cytometer 5 functions as a measuring section which measures the nuclear stained cells (cell number), and a histogram acquiring section which acquires a DNA histogram of the fluorescence intensity by using measurement results of the measuring section.

Data of the DNA histogram obtained by the flow cytometer 5 are transmitted to the PC (analysis controlling unit) 6 constituting the cell analyzing apparatus 2, and stored in a storing unit (for example, a RAM or a flash memory). The data may be displayed on a displaying section (for example, an LCD) of the analysis controlling unit 6.

FIG. 3 shows an example of the DNA histogram acquired by the flow cytometer 5.

The ordinate of the DNA histogram indicates the cell number, and the abscissa indicates the fluorescence intensity corresponding to the DNA amount. A chromosome is formed by DNA, and the staining dye is intercalated into double-stranded DNA. When the fluorescence intensity is measured, therefore, the amount of DNA can be measured.

In FIG. 3, the region indicated by A is a region where substances appear in which chromosomes adhere to debris, i.e., broken cells (dusts) or interstitial tissues. The DNA amount of cells in the region is smaller than that of normal G0/G1 phase cells.

The region indicated by B is a region where groups of G0/G1 phase cells, i.e., cells of a normal DNA amount appear.

The region indicated by C is a region where groups of S phase cells appear. Among groups of S phase cells, a group in which DNA synthesis has just begun has a DNA amount which is slightly larger than that of normal G0/G1 phase cells. The DNA amount continues to increase until the DNA amount of cells reaches the level of G2 phase (G2 phase corresponds to the region indicated by E which will be described later).

The region indicated by D is a region where cell groups of DNA aneuploidy appear. The DNA amount of cells in the region shows a distribution in aneuploids (not integer multiples of the normal DNA amount). The region is often detected in a tumor tissue, and appears in various locations.

The region indicated by E is a region where groups of G2/M phase cells appear. G2 phase cells contain a DNA amount which is two times that of normal G0/G1 phase cells. In M phase cells, a mother cell divides into two daughter cells, and the contained DNA amount is two times that of normal G0/G1 phase cells.

The region indicated by F is a region where cell groups containing another DNA amount appear. In the region, S or G2/M phase cells of cells with DNA aneuploidy are sometimes detected.

The character of P indicates a peak position of the region of B (groups of G0/G1 phase cells). The arrow zone indicated by W shows a peak zone of the region of B (groups of G0/G1 phase cells), and a zone of points corresponding to 5% of the value of the peak P.

When a DNA histogram is to be acquired, the flow cytometer 5 irradiates the cell suspension flowing in the interior of the flow cytometer 5 with laser light, and measures the fluorescence intensity with respect to the laser light. Since cells contain a fluorescent dye as a result of the coloring process, the cells exhibit different light absorptances, and their fluorescence intensities with respect to the laser light are different from one another. The fluorescent dye enters between the double helix of DNA. Therefore, the amount of the entering dye is different depending on the size of DNA. Usually, chromosomes of cancer cells are larger than those of normal cells, and hence cancer cells are larger in amount of dyes which are contained as a result of the coloring process, than normal cells.

Therefore, the waveform of a DNA histogram has a shape showing a feature which is different depending on parameters such as the ratio of normal DNA (cells) contained in the to-be-determined tissue, or that of cancerous DNA (cells).

Next, an analysis data acquiring step of analyzing the thus acquired DNA histogram, and calculating and acquiring data with respect to a plurality of parameters which are described below will be described. The step is processed by the analysis controlling unit 6 of the cell analyzing apparatus.

Alternatively, the apparatus may be configured so that the step is processed by the flow cytometer 5 as described above.

Preferably, the parameters are elements which function as an index for determining a cancer tissue, and which appear as a characteristic pattern in a DNA histogram. Specific examples are (1) the ratio of the number of cells (G0/G1 cells) of a normal DNA amount to the number of all detected cells in a DNA histogram, (2) the ratio (malignancy index) of the number of DNA amplified cells to the number of all detected cells in a DNA histogram, (3) the ratio of the debris number to the number of all detected cells in a DNA histogram, (4) the width (G0/G1 HPCV) of a peak of a normal distribution of cells of a normal DNA amount in a DNA histogram, (5) the area under the curve (AUC) of a waveform which is obtained from a result of a fast Fourier transform of a DNA histogram, and (6) the number of all detected cells in a DNA histogram.

The parameters of (1) to (6) above will be described in accordance with the DNA histogram of FIG. 3.

In (1) above, the ratio of the number of cells (G0/G1 cells) of a normal DNA amount to the number of all detected cells in a DNA histogram means a cell number ratio of groups of G0/G1 phase cells. Namely, the ratio means a ratio of the number of cells appearing in the region of B in the total region.

In (2) above, the ratio (malignancy index) of the number of DNA amplified cells to the number of all detected cells in a DNA histogram means a cell number ratio of groups of S phase cells, cell groups of DNA aneuploidy, groups of G2/M phase cells, and cell groups containing another DNA amount. Namely, the ratio means a ratio of the number of cells appearing in the regions of C, D, E, and F in the total region.

In (3) above, the ratio of the debris number to the number of all detected cells in a DNA histogram means a ratio of the number of cells appearing in the region of A in the total region.

In (4) above, the width (G0/G1 HPCV) of a peak of normal distribution of cells of a normal DNA amount in a DNA histogram shows the peak zone (zone of points corresponding to 5% of the value of the peak P) in the region of B (groups of G0/G1 phase cells), or namely the zone W indicated by the arrow. This represents the degree of dispersion of the peak in the region of B.

Figure 4A:
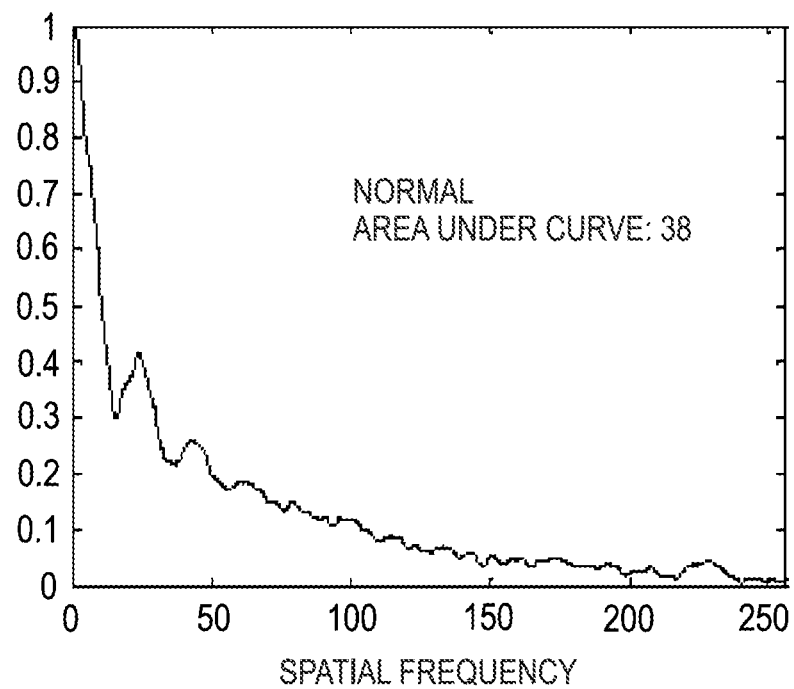
FIGS. 4A and 4B are views showing examples of waveforms which are obtained by FFT processing DNA histograms.
Figure 4B:
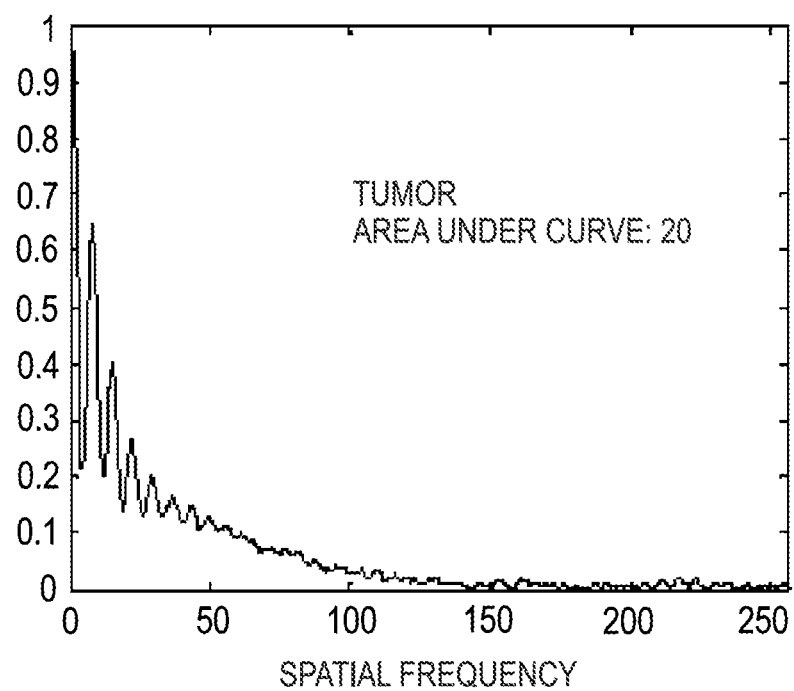

In (5) above, the area under the curve of a waveform which is obtained by a fast Fourier transform of a DNA histogram means the AUC of the FFT-processed waveform of the DNA histogram. FIGS. 4A and 4B show examples of waveforms which are obtained by FFT processing DNA histograms. FIG. 4A shows a waveform obtained by FFT processing a DNA histogram of normal tissues, and FIG. 4B shows a waveform obtained by FFT processing a DNA histogram of cancer tissues. The figures show that the AUCs are 38 and 20, respectively.

In (6) above, the number of all detected cells in a DNA histogram means the cell numbers of debris, groups of G0/G1 phase cells, groups of S phase cells, cell groups of DNA aneuploidy, groups of G2/M phase cells, and cell groups containing another DNA amount. Namely, the ratio means the total number of cells appearing in the all regions or the regions of A to F.

FIGS. 5 to 10 show the distributions of measurement data of the parameters of (1) to (6) above in the case of, for example, colon cancer, respectively. Tissues were taken from patients of colon cancer (26 patients), and measurement data of the parameters of (1) to (6) above were plotted.

Figure 5:
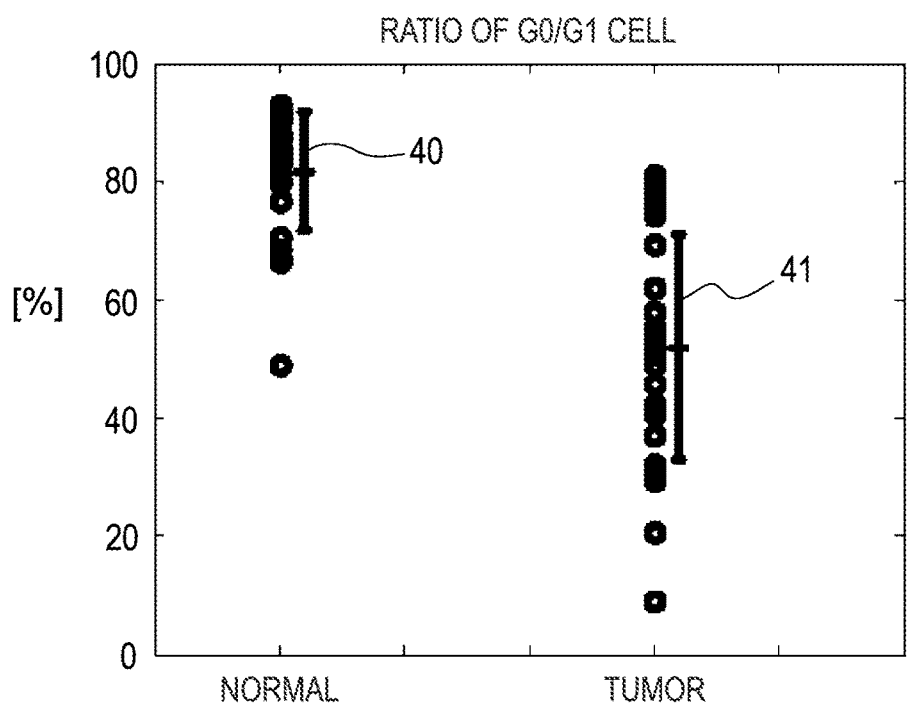
FIG. 5 is a view showing the distribution of a ratio of G0/G1 cells to the number of all detected cells in a DNA histogram.

FIG. 5 shows a view which is obtained by, with respect to each of normal and tumor (cancerous) tissues of the respective patients, measuring the ratio of the number of cells of a normal DNA amount to the number of all detected cells in the DNA histogram of (1), and plotting results of the measurements. As shown in the figure, the ratio of G0/G1 cells (ratio of cells of a normal DNA amount) has a feature that the ratio of tumor (cancerous) tissues is lower than that of normal tissues. The predetermined ranges 40, 41 of the plotted ratios indicate the ranges of the mean value±the standard deviation (mean±SD) of normal tissues and tumor (cancerous) tissues, respectively. The meanings of the predetermined ranges 40, 41 are identical also in FIGS. 6 to 10, 17A and 17B.

Figure 6:
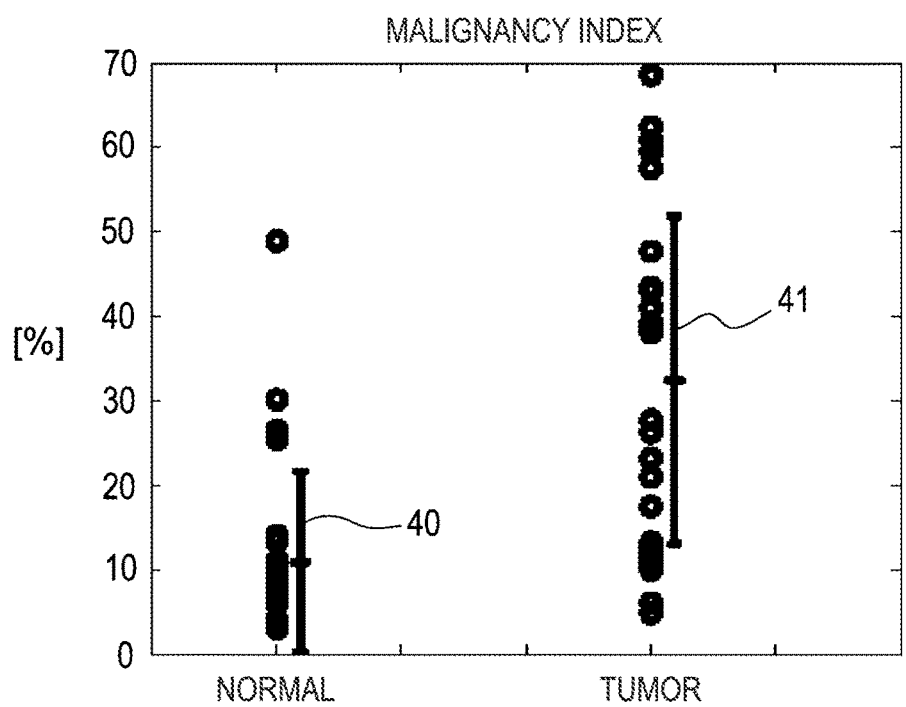
FIG. 6 is a view showing the distribution of the malignancy index with respect to the number of all detected cells in a DNA histogram.

Similarly, FIG. 6 shows a view which is obtained by measuring the ratio (malignancy index) of the number of DNA amplified cells to the number of all detected cells in the DNA histogram of (2), and plotting results of the measurements. As shown in the figure, the malignancy index has a feature that the index of tumor (cancerous) tissues is higher than that of normal tissues.

Figure 7:
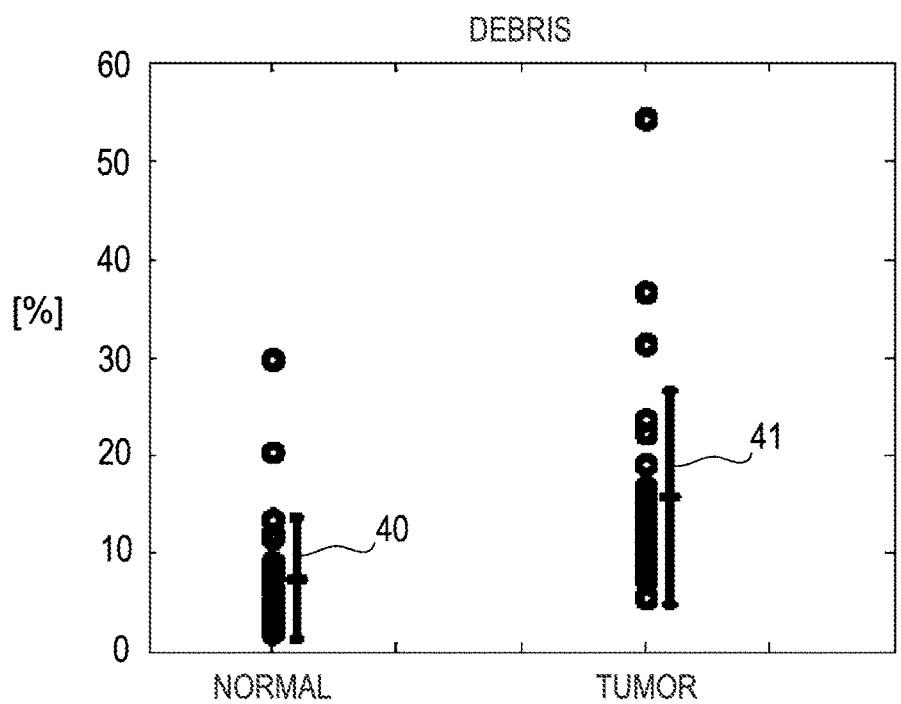
FIG. 7 is a view showing the distribution of a ratio of the debris number to the number of all detected cells in a DNA histogram.

Similarly, FIG. 7 shows a view which is obtained by measuring the ratio of the debris number to the number of all detected cells in the DNA histogram of (3), and plotting results of the measurements. As shown in the figure, the ratio of the debris number has a feature that the ratio of tumor (cancerous) tissues is higher than that of normal tissues.

Figure 8:
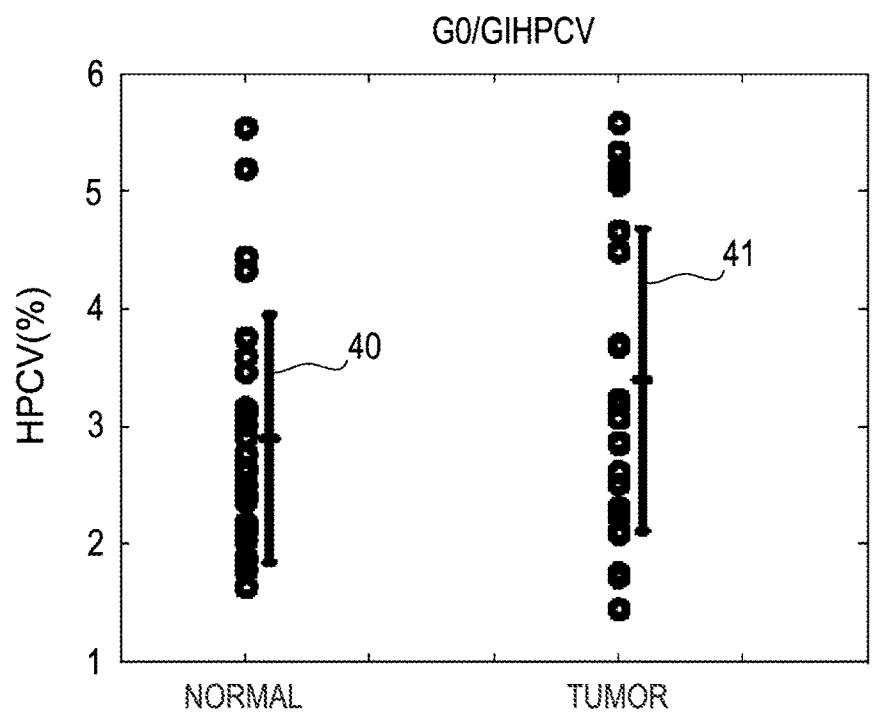
FIG. 8 is a view showing the distribution of the peak width of cells of a normal DNA amount in a DNA histogram.

Similarly, FIG. 8 shows a view which is obtained by measuring the width (G0/G1 HPCV) of a peak of a normal distribution of cells of a normal DNA amount in the DNA histogram of (4), and plotting results of the measurements. As shown in the figure, the G0/G1 HPCV has a feature that the coefficient of tumor (cancerous) tissues is higher than that of normal tissues.

Figure 9:
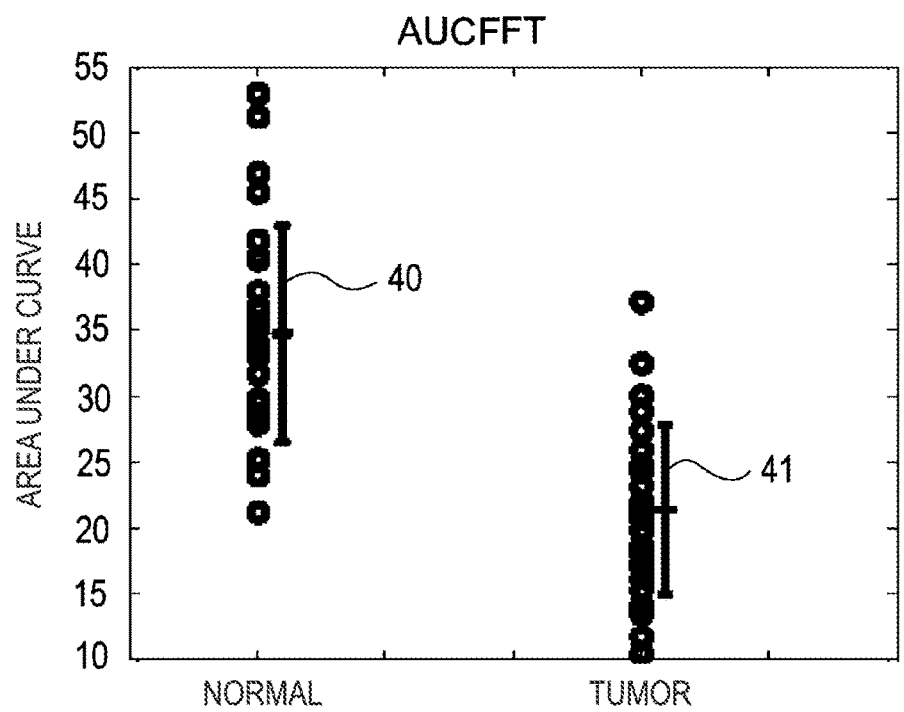
FIG. 9 is a view showing the distribution of the AUC of a waveform which is obtained by FFT processing a DNA histogram.

Similarly, FIG. 9 shows a view which is obtained by calculating the area under the curve A (AUC) of a waveform which is obtained from a result of a fast Fourier transform of the DNA histogram (5), and plotting results of the calculations.

As shown in the figure, the area under the curve has a feature that the area of tumor (cancerous) tissues is smaller than that of normal tissues.

Figure 10:
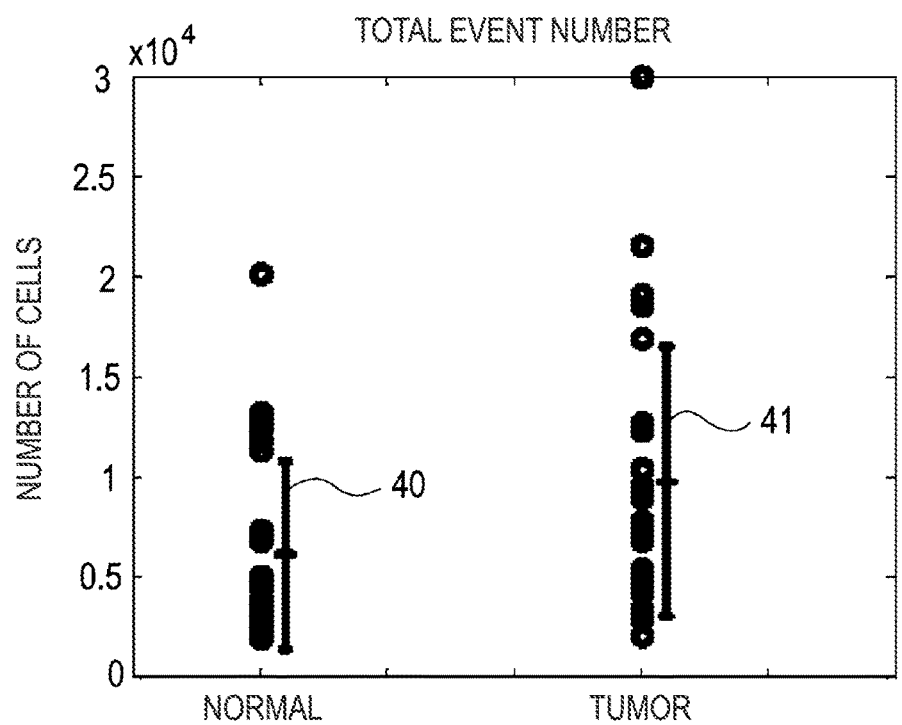
FIG. 10 is a view showing the distribution of the total event number in a DNA histogram.

Similarly, FIG. 10 shows a view which is obtained by measuring the number of all detected cells in the DNA histogram (6), and plotting results of the measurements were plotted. As shown in the figure, the number of all detected cells has a feature that the cell number of tumor (cancerous) tissues is larger than that of normal tissues.

In the above, the parameters of (1) to (6) have been exemplarily described. However, the kinds and numbers of the parameters by which analysis data are calculated or obtained from a histogram may be adequately set. In order to obtain a more accurate result of determination of cancer tissues, it is necessary to use two or more kinds of these parameters. The kinds of parameters are not limited to the above-described ones, and may be any kinds of characteristic parameters which are effective in detecting cancer tissues, and which appear in a histogram.

The data of the parameters which are calculated or obtained as described above are stored in the storing unit (for example, a RAM or a flash memory) of the analysis controlling unit 6.

Next, a parameter determining step will be described in which the thus obtained data of the parameters are compared with optimum thresholds for the parameters to perform a cancer determination on the to-be-determined tissue with respect to each of the parameters. Also this step is processed by the analysis controlling unit 6 of the cell analyzing apparatus 2. Alternatively, the apparatus may be configured so that the step is processed by the flow cytometer 5 as described above. Steps which will be described later, and in which the optimum thresholds are calculated may be performed by another computer based on case data which are previously collected, and the calculated optimum thresholds may be stored in the cell analyzing apparatus 2.

First, the optimum thresholds for the parameters are determined in the following manner by conducting the ROC (Receiver Operating Characteristic) analysis on tissues taken from cancer patients with respect to the parameters of (1) to (6) above.

Tissues are taken from patients of colon cancer (26 patients) as described above, and data (data shown in FIGS. 5 to 10) of the tissues which are acquired for the parameters of (1) to (6) are set as thresholds (cut-off values) for the parameters. The relationships between "sensitivity" and "1-specificity" with respect to each of the thresholds are plotted to form a ROC curve. Here, the sensitivity means the probability of correctly determining cancer tissues as cancer tissues, and the specificity means that of correctly determining normal tissues as normal tissues.

FIGS. 11 to 16 show the ROC curves which are based on the data of FIGS. 5 to 10 with respect the parameters of (1) to (6) above. In each of the figures, the ordinate indicates the sensitivity, and the abscissa indicates the 1-specificity.

Figure 11:
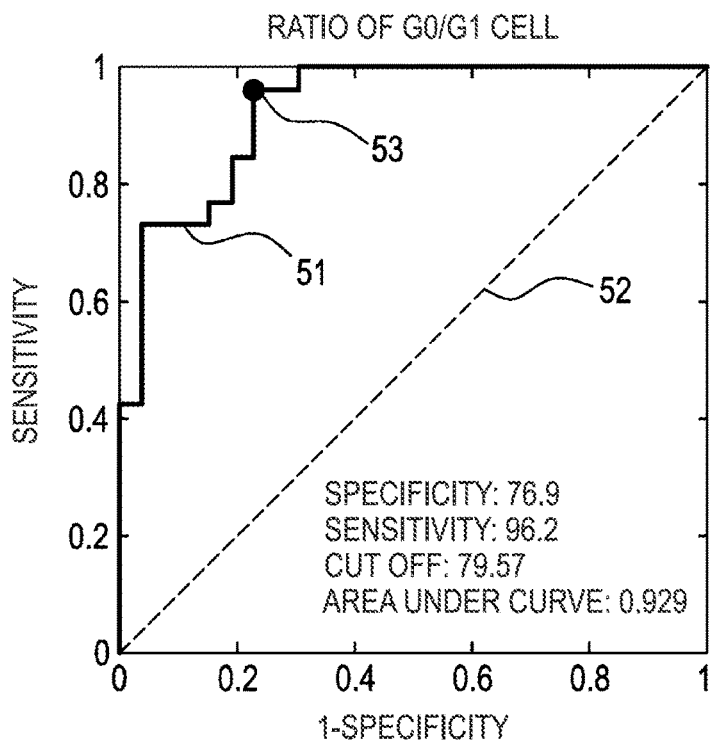
FIG. 11 is a view showing the ROC curve with respect to the ratio of G0/G1 cells.

FIG. 11 is a view showing a ROC curve 51 with respect to the ratio of G0/G1 cells. The figure is based on the data of FIG. 5. In the ROC curve 51, the (26 sets of) obtained data of the ratio of G0/G1 cells are set as the values of the threshold (cut-off), and the relationships between the sensitivity and the 1-specificity with respect to the data are plotted. In the determination of tissues, with respect to the ratio of G0/G1 cells, a tissue which is equal to or larger than the threshold is determined as a normal tissue, and that which is smaller than the threshold is determined as a cancer tissue.

When the threshold is increased, or when the ratio of G0/G1 cells is set high, the sensitivity is raised. The specificity is lowered, and hence the 1-specificity is raised. When the threshold is increased, namely, the probability of correctly determining cancer tissues is increased, but that of correctly determining normal tissues is lowered. In terms of a position on the ROC curve, this corresponds to a position which is near the upper right of the curve.

By contrast, when the threshold is reduced, or when the ratio of G0/G1 cells is set low, the sensitivity is lowered. The specificity is raised, and hence the 1-specificity is lowered. When the threshold is reduced, namely, the probability of correctly determining cancer tissues is lowered, but that of correctly determining normal tissues is raised. In terms of a position on the ROC curve, this corresponds to a position which is near the lower left of the curve.

In the thus obtained ROC curve 51, the optimum threshold is conveniently determined in consideration of the balance between the sensitivity and the specificity. In the embodiment, the optimum threshold is determined by a method using the distance from the upper left corner of the figure. Namely, a point on the ROC curve which is closest to the point (0, 1) in the upper left corner where the sensitivity is 100% and the specificity is 100% is selected, and the threshold at the point is determined as the optimum threshold.

The point on the ROC curve 51 which is selected by the method, and which is closest to the upper left corner is the point 53. The threshold at the point 53, i.e., the optimum threshold is Cut Off: 79.57 [%]. At this time, the sensitivity is Sensitivity: 96.2 [%], and the specificity is Specificity: 76.9 [%].

When the optimum threshold is set to 79.57 [%] in the ROC curve 51 for the ratio of G0/G1 cells, cancer tissues can be correctly determined with a probability of 96.2 [%], and normal tissues can be correctly determined with a probability of 76.9 [%].

In FIG. 11, the area under the ROC curve is AUC: 0.929. The area under the ROC curve is one of indexes for evaluating canceration of the to-be-determined tissue, and has a value of 0.5 to 1.0. The larger area under the ROC curve, the higher accuracy of a cancer determination is obtained.

As another method of determining the optimum threshold in the ROC curve, a method may be employed which uses the Youden index, and in which the point on the ROC curve and remotest from the diagonal broken line 52 of AUC=0.500 is set as the optimum threshold. This is applicable also FIGS. 12 to 16 and 18 below.

Figure 12:
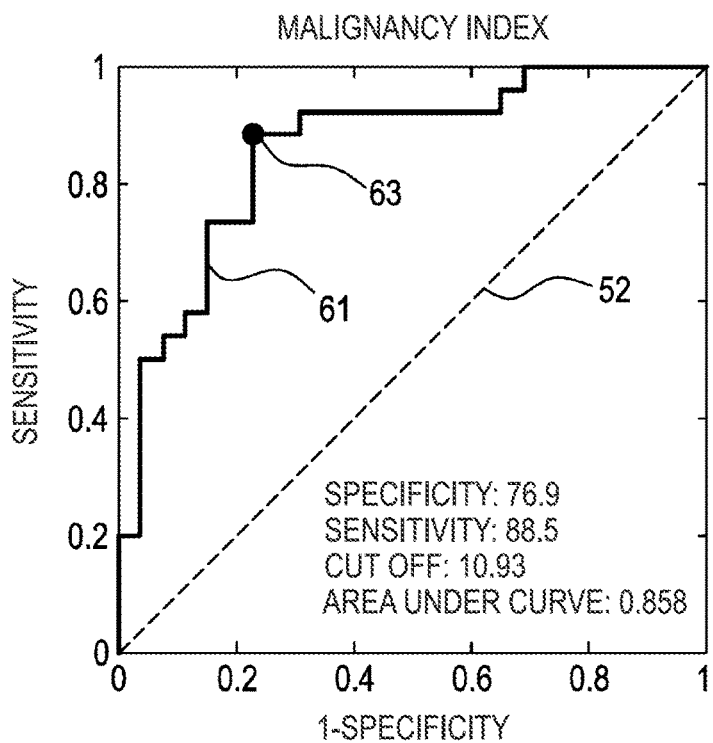
FIG. 12 is a view showing the ROC curve with respect to the malignancy index.

FIG. 12 is a view showing a ROC curve 61 with respect to the malignancy index. The figure is based on the data of FIG. 6. In the ROC curve 61, the (26 sets of) obtained data of the malignancy index are set as the threshold, and the relationships between the sensitivity and the 1-specificity with respect to the data are plotted. In the determination of tissues, with respect to the malignancy index, a tissue which is equal to or larger than the threshold is determined as a cancer tissue, and that which is smaller than the threshold is determined as a normal tissue.

When the threshold is increased, or when the malignancy index is set high, the sensitivity is lowered. The specificity is raised, and hence the 1-specificity is lowered. When the threshold is increased, namely, the probability of correctly determining cancer tissues is lowered, but that of correctly determining normal tissues is increased. In terms of a position on the ROC curve, this corresponds to a position which is near the lower left of the curve.

By contrast, when the threshold is reduced, or when the malignancy index is set low, the sensitivity is raised. The specificity is lowered, and hence the 1-specificity is raised. When the threshold is reduced, namely, the probability of correctly determining cancer tissues is raised, but that of correctly determining normal tissues is lowered. In terms of a position on the ROC curve, this corresponds to a position which is near the upper right of the curve.

In the thus obtained ROC curve 61, a point on the ROC curve 61 which is closest to the upper left corner is the point 63. The threshold at the point 63, i.e., the optimum threshold is Cut Off: 10.93 [%]. At this time, the sensitivity is Sensitivity: 88.5 [%], and the specificity is Specificity: 76.9 [%].

When the optimum threshold is set to 10.93 [%] in the ROC curve 61 for the malignancy index, cancer tissues can be correctly determined with a probability of 88.5 [%], and normal tissues can be correctly determined with a probability of 76.9 [%].

In FIG. 12, the area under the ROC curve is AUC: 0.858.

Figure 13:
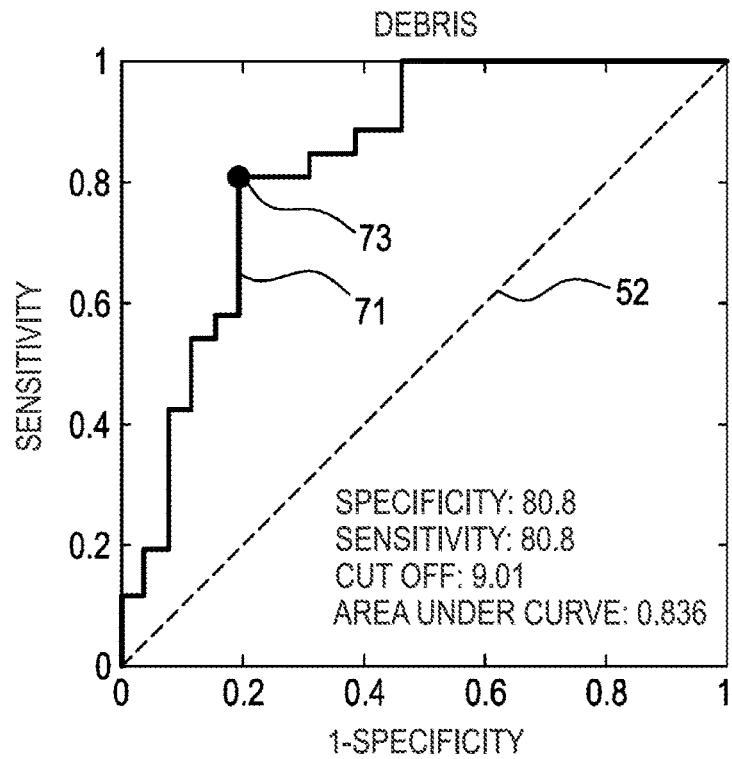
FIG. 13 is a view showing the ROC curve with respect to the debris number.

FIG. 13 is a view showing a ROC curve 71 with respect to debris. The figure is based on the data of FIG. 7. In the ROC curve 71, the (26 sets of) obtained data of the ratio of the debris number are set as the threshold, and the relationships between the sensitivity and the 1-specificity with respect to the data are plotted. In the determination of tissues, with respect to the ratio of the debris number, a tissue which is equal to or larger than the threshold is determined as a cancer tissue, and that which is smaller than the threshold is determined as a normal tissue.

When the threshold is increased, or when the ratio of the debris number is set high, the sensitivity is lowered. The specificity is raised, and hence the 1−specificity is lowered. When the threshold is reduced, namely, or when the ratio of the debris number is set low, the sensitivity is raised. The specificity is lowered, and hence the 1−specificity is raised. Therefore, the characteristics are identical with those which have been described with reference to FIG. 12.

In the thus obtained ROC curve 71, a point on the ROC curve 71 which is closest to the upper left corner is the point 73. The threshold at the point 73, i.e., the optimum threshold is Cut Off: 9.01 [%]. At this time, the sensitivity is Sensitivity: 80.8 [%], and the specificity is Specificity: 80.8 [%].

When the optimum threshold is set to 9.01 [%] in the ROC curve 71 for debris, cancer tissues can be correctly determined with a probability of 80.8 [%], and normal tissues can be correctly determined with a probability of 80.8 [%]

In FIG. 13, the area under the ROC curve is AUC: 0.836.

Figure 14:
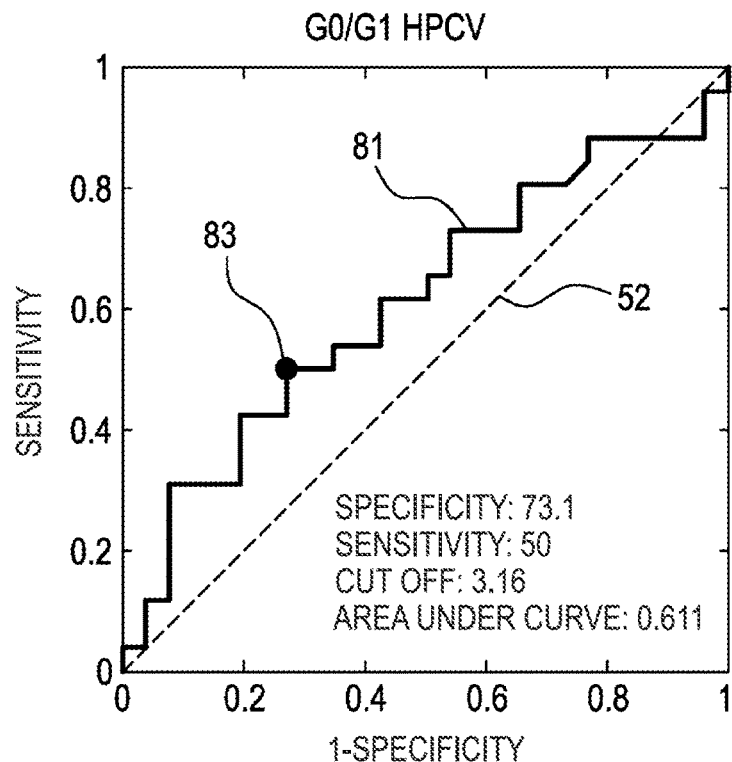
FIG. 14 is a view showing the ROC curve with respect to the peak width of cells of a normal DNA amount.

FIG. 14 is a view showing a ROC curve 81 with respect to the width (G0/G1 HPCV) of a peak of cells of a normal DNA amount.

The figure is based on the data of FIG. 8. In the ROC curve 81, the (26 sets of) obtained data of the G0/G1 HPCV are set as the threshold, and the relationships between the sensitivity and the 1−specificity with respect to the data are plotted. In the determination of tissues, with respect to the G0/G1 HPCV, a tissue which is equal to or larger than the threshold is determined as a cancer tissue, and that which is smaller than the threshold is determined as a normal tissue.

When the threshold is increased, or when the G0/G1 HPCV is set high, the sensitivity is lowered. The specificity is raised, and hence the 1−specificity is lowered. When the threshold is reduced, namely, or when the G0/G1 HPCV is set low, the sensitivity is raised. The specificity is lowered, and hence the 1−specificity is raised. Therefore, the characteristics are identical with those which have been described with reference to FIG. 12.

In the thus obtained ROC curve 81, a point on the ROC curve 81 which is closest to the upper left corner is the point 83. The threshold at the point 83, i.e., the optimum threshold is Cut Off: 3.16 [%]. At this time, the sensitivity is Sensitivity: 50.0 [%], and the specificity is Specificity: 73.1 [%].

When the optimum threshold is set to 3.16 [%] in the ROC curve 81 for the G0/G1 HPCV, cancer tissues can be correctly determined with a probability of 50.0 [%], and normal tissues can be correctly determined with a probability of 73.1 [%].

In FIG. 14, the area under the ROC curve is AUC: 0.611.

Figure 15:
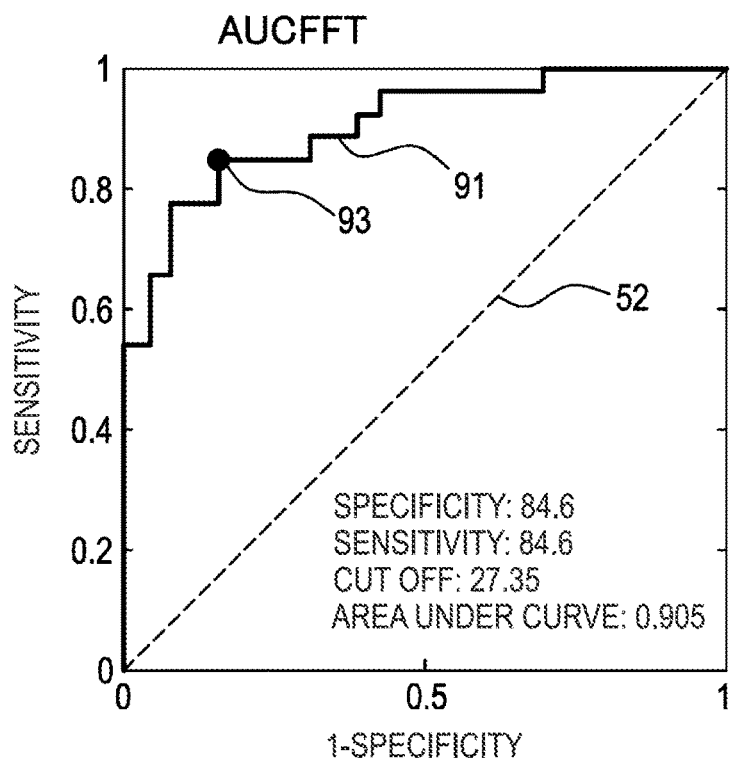
FIG. 15 is a view showing the ROC curve with respect to the AUC FFT.

FIG. 15 is a view showing a ROC curve 91 with respect to the area under the curve (AUC) of a waveform which is obtained by a fast Fourier transform of a DNA histogram. The figure is based on the data of FIG. 9. In the ROC curve 91, the (26 sets of) obtained data of the AUCs are set as the threshold, and the relationships between the sensitivity and the 1−specificity with respect to the data are plotted. In the determination of tissues, with respect to the AUC, a tissue which is equal to or larger than the threshold is determined as a normal tissue, and that which is smaller than the threshold is determined as a cancer tissue.

When the threshold is increased, or when the AUC is set high, the sensitivity is raised. The specificity is lowered, and hence the 1−specificity is raised. When the threshold is reduced, namely, or when the AUC is set low, the sensitivity is lowered. The specificity is raised, and hence the 1−specificity is lowered. Therefore, the characteristics are identical with those which have been described with reference to FIG. 11.

In the thus obtained ROC curve 91, a point on the ROC curve 91 which is closest to the upper left corner is the point 93. The threshold at the point 93, i.e., the optimum threshold is Cut Off: 27.35. At this time, the sensitivity is Sensitivity: 84.6 [%], and the specificity is Specificity: 84.6 [%].

When the optimum threshold is set to 27.35 in the ROC curve 91 for the AUC, cancer tissues can be correctly determined with a probability of 84.6 [%], and normal tissues can be correctly determined with a probability of 84.6 [%].

In FIG. 15, the area under the ROC curve is AUC: 0.905.

Figure 16:
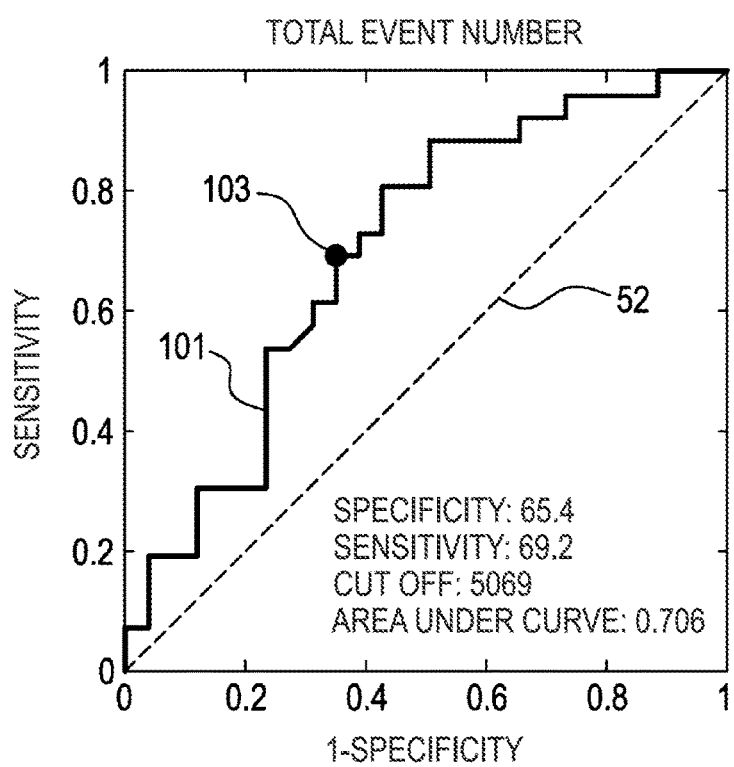
FIG. 16 is a view showing the ROC curve with respect to the total event number.

FIG. 16 is a view showing a ROC curve 101 with respect to the number of all detected cells (total event number). The figure is based on the data of FIG. 10. In the ROC curve 101, the (26 sets of) obtained data of the total event number are set as the threshold, and the relationships between the sensitivity and the 1−specificity with respect to the data are plotted. In the determination of tissues, with respect to the total event number, a tissue which is equal to or larger than the threshold is determined as a cancer tissue, and that which is smaller than the threshold is determined as a normal tissue.

When the threshold is increased, or when the total event number is set high, the sensitivity is lowered. The specificity is raised, and hence the 1−specificity is lowered. When the threshold is reduced, namely, or when the total event number is set low, the sensitivity is raised. The specificity is lowered, and hence the 1−specificity is raised. Therefore, the characteristics are identical with those which have been described with reference to FIG. 12.

In the thus obtained ROC curve 101, a point on the ROC curve 101 which is closest to the upper left corner is the point 103. The threshold at the point 103, i.e., the optimum threshold is Cut Off: 5,069. At this time, the sensitivity is Sensitivity: 69.2 [%], and the specificity is Specificity: 65.4 [%].

When the optimum threshold is set to 5,069 in the ROC curve 101 for the total event number, cancer tissues can be correctly determined with a probability of 69.2 [%], and normal tissues can be correctly determined with a probability of 65.4 [%].

In FIG. 16, the area under the ROC curve is AUC: 0.706.

The thus obtained data of the optimum thresholds, sensitivities, specificities, areas under the ROC curve, ROC curves, and the like for the parameters are stored in the storing unit (for example, a RAM or a flash memory) of the analysis controlling unit 6.

With respect to the to-be-determined tissue, then, the data for the parameters acquired from the histogram of the tissue are compared with the optimum thresholds (optimum cut off values) which are determined as described above, and a cancer determination is performed for each of the parameters.

With respect to the ratio of the number of cells (G0/G1 cells) of a normal DNA amount for the parameter of (1), specifically, the ratio of the number of G0/G1 cells in the to-be-determined tissue is compared with the optimum threshold of 79.57% which is determined as described above. In the case where the ratio is equal to or larger than the optimum threshold of 79.57%, the to-be-determined tissue is determined as a normal tissue. By contrast, in the case where the ratio is smaller than the optimum threshold of 79.57%, the to-be-determined tissue is determined as a cancer tissue.

With respect to the ratio (malignancy index) of the number of DNA amplified cells for the parameter of (2), in the case where the malignancy index of the to-be-determined tissue is equal to or larger than the optimum threshold of 10.93%, the to-be-determined tissue is determined as a cancer tissue. By contrast, in the case where the index is smaller than the optimum threshold of 10.93%, the to-be-determined tissue is determined as a normal tissue.

With respect to the ratio of the debris number for the parameter of (3), in the case where the ratio of the debris number of the to-be-determined tissue is equal to or larger than the optimum threshold of 9.01%, the to-be-determined tissue is determined as a cancer tissue. By contrast, in the case where the ratio is smaller than the optimum threshold of 9.01%, the to-be-determined tissue is determined as a normal tissue.

With respect to the width (G0/G1 HPCV) of a peak for the parameter of (4), in the case where the G0/G1 HPCV of the to-be-determined tissue is equal to or larger than the optimum threshold of 3.16%, the to-be-determined tissue is determined as a cancer tissue. By contrast, in the case where the G0/G1 HPCV is smaller than the optimum threshold of 3.16%, the to-be-determined tissue is determined as a normal tissue.

With respect to the AUC for the parameter of (5), in the case where the AUC of the to-be-determined tissue is equal to or larger than the optimum threshold of 27.35, the to-be-determined tissue is determined as a normal tissue. By contrast, in the case where the AUC is smaller than the optimum threshold of 27.35, the to-be-determined tissue is determined as a cancer tissue.

With respect to the number of all detected cells (total event number) for the parameter of (6), in the case where the total event number of the to-be-determined tissue is equal to or larger than the optimum threshold of 5,069, the to-be-determined tissue is determined as a cancer tissue. By contrast, in the case where the number is smaller than the optimum threshold of 5,069, the to-be-determined tissue is determined as a normal tissue.

Next, the scoring processing step will be described in which, with respect to the result of the cancer determination for each of the parameters, scoring is conducted for the parameter. This step is processed by the analysis controlling unit 6. Alternatively, the system may be configured so that the step is processed by the flow cytometer 5.

The scoring process means a work in which scoring is conducted for each of the parameters depending on whether the to-be-determined tissue is determined as a cancer tissue or a normal tissue in the cancer determination for each of the parameters, i.e., based on information of the result of the cancer determination for each of the parameters.

Specifically, the scoring process is conducted in the following manner. In the case where the result of the cancer determination for one of the parameters shows that the to-be-determined tissue is a cancer tissue, specifically, the score of the to-be-determined tissue for the parameter is set to +1, and, in the case where the result shows that the tissue is a normal tissue, the score is set to 0. The scoring process is conducted for each of the parameters (1) to (6).

Next, an overall determining step (score combination determining step) in which results of the parameters are combined with one another and a cancer determination is overall performed on the to-be-determined tissue will be described. Also the step is processed by the analysis controlling unit 6. Alternatively, the apparatus may be configured so that the step is processed by the flow cytometer 5.

The scores of the parameters which are scored in the scoring processing step are totalized (for example, added to one another), whereby analysis data relating to a plurality of parameters are combined with one another to calculate the overall score of the to-be-determined tissue.

Then, a cancer determination based on the calculated overall score, i.e., an overall cancer determination in which the results of the parameters are combined with one another is performed. The determination is performed by comparing the calculated overall score of the to-be-determined tissue with a predetermined optimum threshold for the overall score.

The optimum threshold for the overall score is determined by performing a ROC analysis on the overall score of tissues taken from cancer patients.

Figures 17A, 17B:
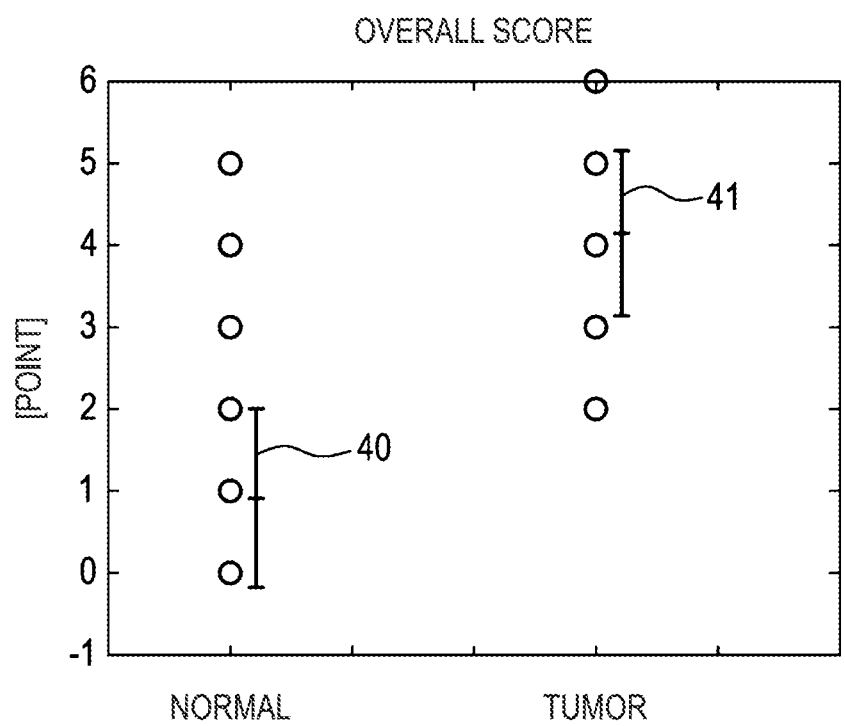
FIG. 17A is a table showing the distribution of an overall score calculated with respect to tissues taken from cancer patients.
FIG. 17B is a graph where the distribution of the overall score is plotted.

FIG. 17A is a table showing the distribution of an overall score calculated with respect to tissues taken from patients of colon cancer (26 patients), and FIG. 17B is a graph where the distribution of the overall score is plotted.

As shown in the figure, the overall score has a feature that the overall score of tumor (cancerous) tissues is higher than that of normal tissues.

The overall scores (overall score shown in FIGS. 17A and 17B) of the tissues taken from patients of colon cancer (26 patients) are set as thresholds (cut-off values). The relationships between "sensitivity" and "1-specificity" with respect to each of the thresholds are plotted to form a ROC curve in a similar manner as FIGS. 11 to 16 described above.

Figure 18:
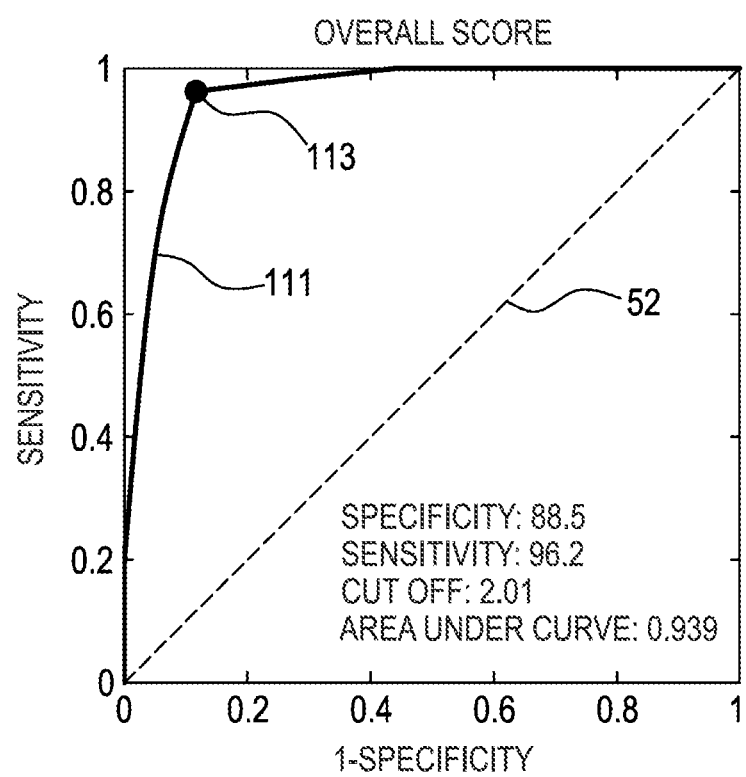
FIG. 18 is a view showing the ROC curve with respect to an overall score.

FIG. 18 shows the ROC curve of the overall score which is based on the data of FIGS. 17A and 17B. In the determination of tissues, with respect to the overall score, a tissue which is equal to or larger than the threshold is determined as a cancer tissue, and that which is smaller than the threshold is determined as a normal tissue.

When the threshold is increased, or when the overall score is set high, the sensitivity is lowered. The specificity is raised, and hence the 1-specificity is lowered. When the threshold is reduced, namely, when the overall score is set low, the sensitivity is raised. The specificity is lowered, and hence the 1-specificity is raised. Therefore, the characteristics are identical with those which have been described with reference to FIG. 12.

In the thus obtained ROC curve 111, a point on the ROC curve 111 which is closest to the upper left corner (position of coordinate (0, 1)) of FIG. 18 is the point 113. The threshold at the point 113 is the optimum threshold, and its value is Cut Off: 2.01 [points]. At this time, the sensitivity is Sensitivity: 96.2 [%], and the specificity is Specificity: 88.5 [%].

When the optimum threshold is set to 2.01 [points], namely, cancer tissues can be correctly determined with a probability of 96.2 [%], and normal tissues can be correctly determined with a probability of 88.5 [%].

In FIG. 18, the area under the ROC curve is AUC: 0.939.

The data of the optimum thresholds, sensitivity, specificity, area under the ROC curve, ROC curve, and the like for the thus determined overall score are stored in the storing unit (for example, a RAM or a flash memory) of the analysis controlling unit 6.

With respect to the to-be-determined tissue, the overall score in which results of the parameters acquired from the histogram of the tissue are combined together is compared with the optimum threshold (optimum cut off value) which is determined as described above, whereby a cancer determination is performed on the tissue.

Specifically, the overall score of the to-be-determined tissue is compared with the optimum threshold of 2.01 which is determined as described above. In the case where the score is equal to or larger than the optimum threshold of 2.01 points, the tissue is determined as a cancer tissue. By contrast, in the case where the score is smaller than the optimum threshold of 2.01 points, the tissue is determined as a normal tissue.

When the optimum thresholds (FIGS. 11 to 16) in the ROC curves of the single parameters which are described in the above-described method are compared with the optimum threshold (FIG. 18) in the ROC curves of the overall score in which results of the parameters are combined with one another, the optimum threshold for the overall score has an obviously higher value in the balance between the sensitivity and the specificity, and also in the area under the ROC curve.

When an overall cancer determination in which results of a plurality of parameters are combined with one another is performed, therefore, the accuracy of a cancer determination can be remarkably improved as compared to a cancer determination based on single parameters. Moreover, a determination can be performed by comparison with the optimum threshold (an example of the threshold of predetermined parameters) which is calculated based on case data that are previously collected, and which is stored in the cell analyzing apparatus 2. Therefore, a determination can be performed more rapidly and adequately.

With respect to a plurality of characteristic parameters in the histogram, results of the cancer determination for the parameters are scored, and a cancer determination is performed based on the overall score in which the scores are combined together. Therefore, a correct determination can be performed by an overall cancer determination, also on a cancer tissue exhibiting a special pattern of a DNA histogram which does not represent a feature with respect to a part of parameters.

Next, weighting relating to scoring for each parameter will be described.

In the above-described scoring processing step, weighting may be conducted among parameters in the scoring performed for each of the parameters.

With respect to a parameter which shows a high cancer determination accuracy among a plurality of parameters, in the case where a tissue is determined as a cancer tissue in a cancer determination for the parameter, specifically, a score which is higher than scores for the other parameters may be provided to the parameter. Namely, different scorings may be performed among the parameters based on the degree of contribution to the cancer determination.

When this is applied to the characteristics of the ROC curve, with respect to a parameter which is well balanced in sensitivity and specificity, and which has a position (optimum threshold) that is particularly near the upper left corner is assigned a high score in the case where it is determined in a cancer determination that the questioned tissue is a cancer tissue.

When such weighting is conducted, a tissue which is determined as a cancer tissue by using a parameter of a high accuracy of a cancer determination is determined as a cancer tissue with a higher probability in the cancer determination based on the overall score. Moreover, also the AUC of the overall score ROC curve is increased, and the accuracy of a cancer determination is enhanced.

According to an aspect of the presently disclosed subject matter, a plurality of characteristic parameters of the histogram acquired from a tissue which is the target of the determination (hereinafter, such a tissue is referred to as the to-be-determined tissue) are detected, a cancer determination is performed for each of the parameters, and an overall determination of cancer is performed based on an overall score which is obtained by scoring results of the determinations, and combining features of the parameters. Therefore, the difference between cancer and normal tissues is made clear, and cancerous tissues can be distinguished more accurately.

The presently disclosed subject matter is not limited to the above-exemplified embodiment, and may be adequately changed without departing from the spirit of the invention.

What is claimed is:

1. A method of analyzing cells, the method comprising:
   measuring a number of cells which are nuclear stained, in a to-be-determined tissue, and acquiring a histogram showing a fluorescence intensity based on a result of the measurement;
   analyzing the histogram, and acquiring data of predetermined parameters, the parameters being related to a number of cells and/or the histogram;
   comparing the data of the parameters with first thresholds predetermined for the parameters, to perform a first cancer determination for each of the parameters on the to-be-determined tissue;
   performing a scoring process for each of the parameters, on a result of the first cancer determination for each of the parameters, to calculate scores of the parameters; and
   combining the scores of the parameters with one another, thereby performing a second cancer determination on the to-be-determined tissue.

2. The method according to claim 1, wherein the second cancer determination is a determination that is performed by comparing an overall score in which the scores of the parameters are totalized, with a predetermined second threshold.

3. The method according to claim 2, wherein the second threshold is a value of an overall score that, in the overall score which is previously acquired, in a ROC curve in which a sensitivity indicating a probability of correctly determining a cancer tissue, and a specificity indicating a probability of correctly determining a normal tissue are plotted, is determined in consideration of a balance between the sensitivity and the specificity.

4. The method according to claim 1, wherein the first thresholds are values of analysis data that, in a large number of analysis data for the parameters which are previously acquired, in a ROC curve in which a sensitivity indicating a probability of correctly determining a cancer tissue, and a specificity indicating a probability of correctly determining a normal tissue are plotted, are determined in consideration of a balance between the sensitivity and the specificity.

5. The method according to claim 1, wherein the scoring process is a process in which scoring is performed based on information of a result of the first cancer determination for each of the parameters.

6. The method according to claim 5, wherein, in the scoring, weighting is performed among the parameters based on a degree of contribution to the second cancer determination.

7. The method according to claim 1, wherein the parameters include at least two or more of: a ratio of a number of all cells of a normal DNA amount to a number of all cells in the histogram; a ratio of a number of DNA amplified cells to a number of all cells in the histogram; a ratio of a debris number to a number of all cells in the histogram; a width of a peak of a normal distribution of cells of a normal DNA amount in the histogram; an area under a curve of a waveform which is obtained by performing a fast Fourier transform of the histogram; and a number of all cells in the histogram.

8. An apparatus for analyzing cells, the apparatus comprising:
a flow cytometer which is configured to measure a number of cells which are nuclear stained, and which is configured to acquire a histogram showing a fluorescence intensity based on a result of the measurement; and
an analysis controlling unit:
which is configured to analyze the histogram acquired by the flow cytometer;
which is configured to acquire data of predetermined parameters, the parameters being related to a number of cells and/or the histogram;
which is configured to perform a determination of a cancer or normal tissue, with respect to the acquired data based on thresholds predetermined for the parameters;
which is configured to perform a scoring process for each of the parameters, on a result of determination of a cancer or normal tissue for each of the parameters, to calculate scores of the parameters;
which is configured to combine the scores of the parameters with one another; and
which is configured to perform a determination of a cancer or normal tissue based on the combined scores.

* * * * *